US012672856B2

(12) United States Patent
Kim et al.

(10) Patent No.: US 12,672,856 B2
(45) Date of Patent: Jul. 7, 2026

(54) ULTRASONIC IMAGE PROCESSING DEVICE, IMAGE PROCESSING METHOD THEREOF, SYSTEM AND PROGRAM

(71) Applicant: GODIUS CO., LTD., Seoul (KR)

(72) Inventors: Sun Kim, Seoul (KR); Si Yong Seong, Seoul (KR); Hyun Sook Lee, Seoul (KR); Tae Hyun Hwang, Seoul (KR); Dong Hwan Kang, Seoul (KR); Hyun Sup Park, Seoul (KR)

(73) Assignee: Godius Co., Ltd., Seoul (KR)

( * ) Notice: Subject to any disclaimer, the term of this patent is extended or adjusted under 35 U.S.C. 154(b) by 0 days.

(21) Appl. No.: 18/396,492

(22) Filed: Dec. 26, 2023

(65) Prior Publication Data

US 2025/0099079 A1 Mar. 27, 2025

(30) Foreign Application Priority Data

Sep. 25, 2023 (KR) ........................ 10-2023-0127717

(51) Int. Cl.
*A61B 8/00* (2006.01)

(52) U.S. Cl.
CPC ............ *A61B 8/5207* (2013.01); *A61B 8/461* (2013.01)

(58) Field of Classification Search
CPC ............................... A61B 8/5207; A61B 8/461
See application file for complete search history.

(56) References Cited

U.S. PATENT DOCUMENTS 11,301,997 B2 * 4/2022 Majeed .................. A61B 5/055
2013/0296743 A1 * 11/2013 Lee ........................ G16H 50/30
601/3

(Continued)

FOREIGN PATENT DOCUMENTS

CN          104093452 A      10/2014
JP        2017023498 A       2/2017
(Continued)

OTHER PUBLICATIONS

Korean Intellectual Property Office, Notice of Office Action, May 14, 2024.

(Continued)

*Primary Examiner* — Joel Lamprecht
*Assistant Examiner* — James F McDonald, III
(74) *Attorney, Agent, or Firm* — Leydig, Voit & Mayer, Ltd.

(57) ABSTRACT

The present disclosure may include: a communication module configured to perform communication with an ultrasonic irradiation device, an ultrasonic imaging device, and a display device; and a processor configured to control an operation in relation to ultrasonic image processing, and the processor is configured to: receive an ultrasonic image from the ultrasonic imaging device through the communication module; extract an irradiation area image for a region of interest (ROI) in the ultrasonic image of the ultrasonic imaging device associated with an ultrasonic irradiation signal of the ultrasonic irradiation device; correct the irradiation area image based on a variation of the ultrasonic irradiation signal in the irradiation area image in a state of focused ultrasound of the ultrasonic irradiation device; and control the display device to display the corrected irradiation area image on the display device.

11 Claims, 8 Drawing Sheets

(56) References Cited

U.S. PATENT DOCUMENTS

| | | | |
|---|---|---|---|
| 2014/0316269 A1* | 10/2014 | Zhang | A61B 8/4209 602/1 |
| 2015/0080715 A1* | 3/2015 | Deno | A61B 8/463 600/424 |
| 2015/0080725 A1* | 3/2015 | Wegner | G01S 15/8997 600/443 |
| 2016/0113620 A1 | 4/2016 | Slayton et al. | |
| 2017/0027645 A1* | 2/2017 | Ben Oren | A61N 5/0625 |
| 2018/0308221 A1* | 10/2018 | Ichikawa | A61B 8/54 |
| 2020/0315574 A1* | 10/2020 | Nanaumi | A61B 5/708 |
| 2020/0342591 A1* | 10/2020 | Majeed | A61B 5/055 |
| 2023/0062672 A1* | 3/2023 | Hyun | A61B 8/5207 |
| 2023/0119063 A1 | 4/2023 | Gardner et al. | |
| 2023/0129687 A1* | 4/2023 | Regensburger | A61B 6/5205 601/2 |
| 2023/0211187 A1 | 7/2023 | Degertekin et al. | |

FOREIGN PATENT DOCUMENTS

| | | |
|---|---|---|
| KR | 10-2009-0115728 A | 11/2009 |
| KR | 20120054920 A | 5/2012 |

OTHER PUBLICATIONS

Taiwan Intellectual Property Bureau of the Ministry of Economic Affairs, Notice of Office Action, Apr. 2, 2024.
French Search Report and Written Opinion regarding Application No. 2315101, Nov. 15, 2024.

* cited by examiner

1000

10

100

20

30

FIG. 5
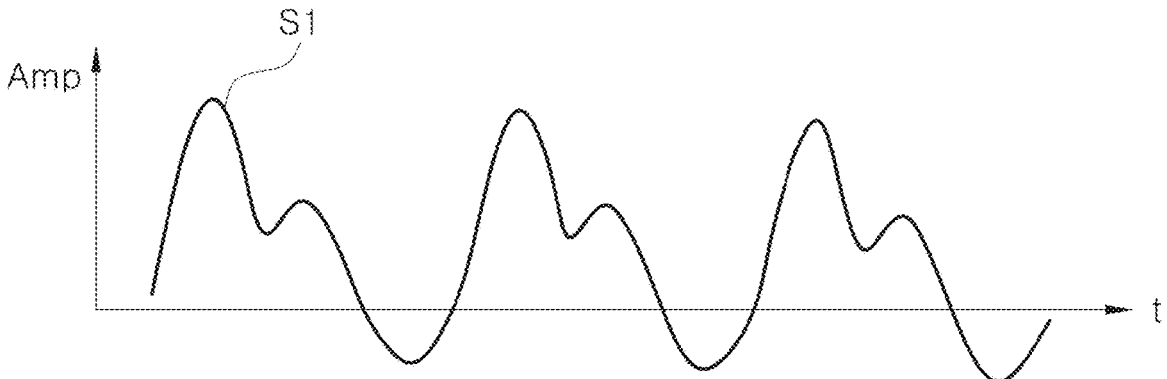
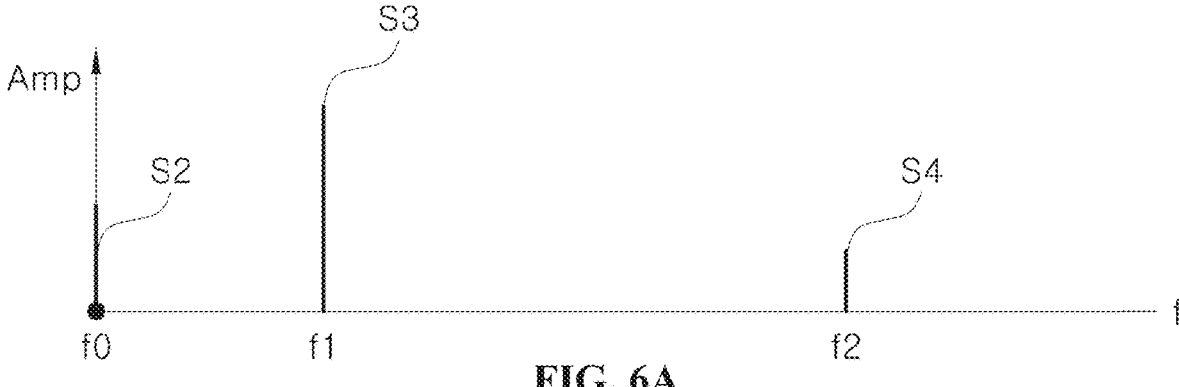
FIG. 6A
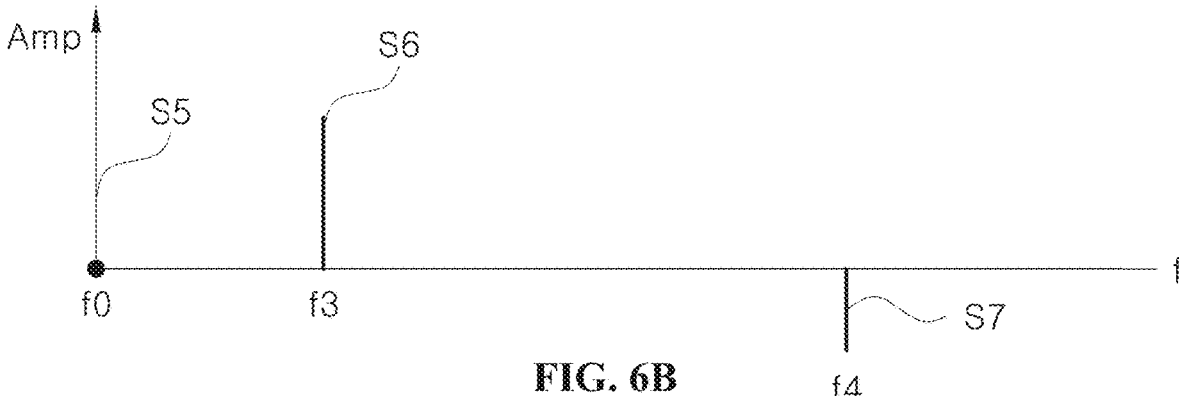
FIG. 6B

ULTRASONIC IMAGE PROCESSING DEVICE, IMAGE PROCESSING METHOD THEREOF, SYSTEM AND PROGRAM

CROSS-REFERENCE TO RELATED APPLICATIONS

A claim for priority under 35 U.S.C. § 119 is made to Korean Patent Application No. 10-2023-0127717 filed on Sep. 25, 2023, in the Korean Intellectual Property Office, the entire contents of which are hereby incorporated by reference.

BACKGROUND

1. Technical Field

The present disclosure relates to an ultrasonic image processing device, an image processing method thereof, a system, and a program.

2. Description of Related Art

Ultrasound refers to a wave with a frequency of 20 kHz or higher and has the property of penetrating water, and is widely used in medical fields such as an ultrasonic diagnostic device and an ultrasonic therapy device.

The most representative use of ultrasound in the medical field is an ultrasound imaging device using the transmission and reflection properties of ultrasound. For example, a device visualizes the reflected time and degree of intensity of ultrasound by transmitting the ultrasound through the organs of a human body and acquires sectional images within the human body.

Furthermore, a device burns off specific subcutaneous tissues such as tumors in the skin by using heat generated by a high intensity focused ultrasound (HIFU) or causes degeneration and regeneration of skin tissues.

However, a conventional device using ultrasound has limitations in efficiently monitoring the position on which ultrasound is focused and the process of degenerating tumors, so there is a limit in preventing a safety accident caused by inaccuracies in ultrasonic irradiation and focusing while improving the accuracy of ultrasonic irradiation and focusing.

PRIOR ART LITERATURE (Patent Document 1) Korean Patent Publication No. 10-2009-0115728 (published on Nov. 5, 2009)

SUMMARY

According to the embodiment of the present disclosure, the position on which ultrasound is focused and the process of degenerating tumors are efficiently monitored, and thus a safety accident caused by inaccuracies in ultrasonic irradiation and focusing can be prevented while improving the accuracy of ultrasonic irradiation and focusing.

Technical problems of the inventive concept are not limited to the technical problems mentioned above, and other technical problems not mentioned will be clearly understood by those skilled in the art from the following description.

An ultrasonic image processing device according to an aspect of the present disclosure may include: a communication module configured to perform communication with an ultrasonic irradiation device, an ultrasonic imaging device, and a display device; and a processor configured to control an operation in relation to ultrasonic image processing, and the processor is configured to: receive an ultrasonic image from the ultrasonic imaging device through the communication module; extract an irradiation area image for a region of interest (ROI) in the ultrasonic image of the ultrasonic imaging device associated with an ultrasonic irradiation signal of the ultrasonic irradiation device; correct the irradiation area image based on a variation of the ultrasonic irradiation signal in the irradiation area image in a state of focused ultrasound of the ultrasonic irradiation device; and control the display device to display the corrected irradiation area image on the display device.

Furthermore, the processor may extract the irradiation area image based on an amplitude and phase data.

Furthermore, the processor may correct a brightness of the irradiation area image to a preset level.

Furthermore, the processor may correct an edge of the irradiation area image to a preset level.

Furthermore, the processor may further control the display device to display a degeneration area image in the corrected irradiation area image on the display device.

Furthermore, an ultrasonic image processing method performed by an ultrasonic image processing device according to another aspect of the present disclosure may include: receiving an ultrasonic image from an ultrasonic imaging device; extracting an irradiation area image for a region of interest (ROI) in the ultrasonic image of the ultrasonic imaging device associated with an ultrasonic irradiation signal of an ultrasonic irradiation device; correcting the irradiation area image based on a variation of the ultrasonic irradiation signal in the irradiation area image in a state of focused ultrasound of the ultrasonic irradiation device; and controlling a display device to display the corrected irradiation area image on the display device.

Furthermore, the operation of correcting the irradiation area image may include correcting a brightness of the irradiation area image to a preset level.

Furthermore, the operation of correcting the irradiation area image may include correcting an edge of the irradiation area image to a preset level.

Furthermore, the operation of controlling the display device may further include controlling the display device to display a degeneration area image in the corrected irradiation area image on the display device.

Furthermore, an ultrasonic image providing system according to still another aspect of the present disclosure may include: an ultrasonic irradiation device; an ultrasonic imaging device; a display device; and an ultrasonic image processing device configured to perform communication with the ultrasonic irradiation device, the ultrasonic imaging device, and the display device, and the ultrasonic image processing device is configured to: receive an ultrasonic image from the ultrasonic imaging device; extract an irradiation area image for a region of interest (ROI) in the ultrasonic image of the ultrasonic imaging device associated with an ultrasonic irradiation signal of the ultrasonic irradiation device; correct the irradiation area image based on a variation of the ultrasonic irradiation signal in the irradiation area image in a state of focused ultrasound of the ultrasonic irradiation device; and control the display device to display the corrected irradiation area image on the display device.

In addition to the above, a computer program stored in a computer-readable recording medium for implementing the present disclosure may be further provided.

In addition to the above, a computer-readable recording medium recording a computer program for implementing the present disclosure may be further provided.

BRIEF DESCRIPTION OF THE FIGURES

FIGS. 3 to 9 are diagrams illustrating an ultrasonic image processing process according to the present disclosure.

DETAILED DESCRIPTION

Figure 1:
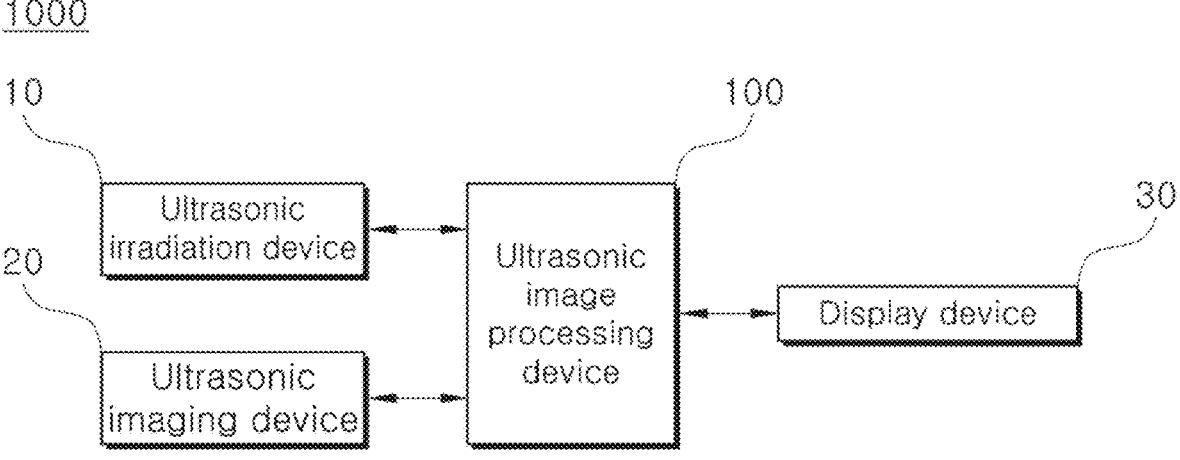
FIG. 1 is a diagram illustrating an example of an ultrasonic image providing system according to the present disclosure.

In the drawings, a same reference numeral designates a same element. The present disclosure does not describe all elements of embodiments, and general contents in the technical field to which the present disclosure belongs or repeated contents of the embodiments will be omitted. The terms, such as "unit, module, member, and block" may be embodied as hardware or software, and a plurality of "units, modules, members, and blocks" may be implemented as one element, or "a unit, a module, a member, or a block" may include a plurality of elements.

Throughout the present disclosure, when a part is referred to as being "connected" to another part, this includes direct connection and indirect connection, and the indirect connection may include connection via a wireless communication network.

Furthermore, when a certain part "includes" a certain element, other elements are not excluded unless explicitly described otherwise, and other elements may be included.

In the entire specification of the present disclosure, when any member is located "on" another member, this includes a case in which still another member is present between both members as well as a case in which one member is in contact with another member.

It will be understood that terms such as "first" and "second" may be used in the specification to distinguish an element from another element, and the elements are not restricted by the above terms.

A singular expression includes a plural expression unless there is a clear exception in the context.

An identification code in each of operational steps is used for the convenience of description and not for describing the order of the operational steps, and the operational steps may be implemented differently from the order described unless there is a specific order explicitly described in the context.

Hereinafter, the operational principle and the embodiments of the present disclosure will be described with reference to the accompanying drawings.

In the specification of the present disclosure, the ultrasonic image processing device may include various types of devices capable of performing an operational process and providing a result to a user. For example, the ultrasonic image processing device according to the present disclosure may include all or either one of a computer, a server device, and a portable terminal.

Herein, the computer may include, for example, a notebook computer, a desktop computer, a laptop computer, a tablet PC, a slate PC, or the like in which a web browser is provided.

The server device is a server of performing communication with an external device and processing information and may include an application server, a computing server, a database server, a file server, a mail server, a proxy server, a web server, or the like.

The portable terminal is a wireless communication device that secures portability and mobility and may include all types of handheld-based wireless communication device such as a terminal of Personal Communication System (PCS), Global System for Mobile communications (GSM), Personal Digital Cellular (PDC), Personal Handyphone System (PHS), Personal Digital Assistant (PDA), International Mobile Telecommunication (IMT)-2000, Code Division Multiple Access (CDMA)-2000, W-Code Division Multiple Access (W-CDMA), and Wireless Broadband Internet (Wi-Bro), or a smartphone, and a wearable device such as a watch, a ring, a bracelet, an anklet, a necklace, eyeglasses, a contact lens, or a head-mounted-device (HMD).

An ultrasonic image providing system according to the present disclosure may receive an ultrasonic image from the ultrasonic imaging device, extract an irradiation area image for a region of interest (ROI) in the ultrasonic image of the ultrasonic imaging device associated with an ultrasonic irradiation signal of the ultrasonic irradiation device, correct the irradiation area image based on a variation amount of the ultrasonic irradiation signal in the irradiation area image in a state of focused ultrasound, and control the display device to display the corrected irradiation area image on the display device.

According to the ultrasonic image providing system according to the present disclosure, the position on which ultrasound is focused and the process of degenerating tumors are efficiently monitored, a safety accident caused by inaccuracies in ultrasonic irradiation and focusing can be prevented while improving the accuracy of ultrasonic irradiation and focusing.

Hereinafter, the ultrasonic image providing system will be described in detail.

Figure 2:
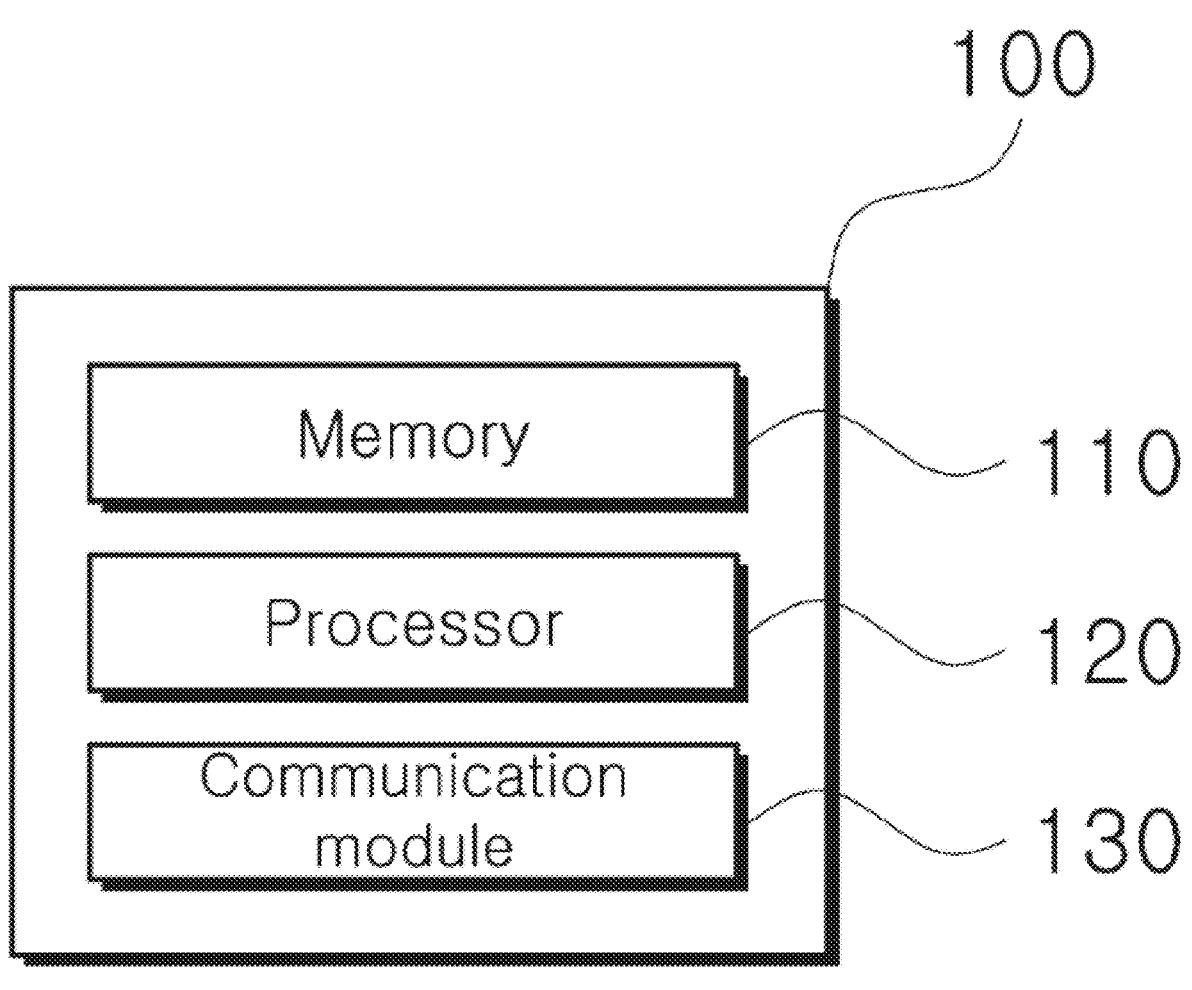
FIG. 2 illustrates the configuration of an ultrasonic image processing device shown in FIG. 1.

FIG. 1 is a diagram illustrating an example of an ultrasonic image providing system according to the present disclosure. FIG. 2 illustrates the configuration of an ultrasonic image processing device shown in FIG. 1.

Referring to FIG. 1 and FIG. 2, an ultrasonic image providing system 1000 may include an ultrasonic irradiation device 10, an ultrasonic imaging device 20, a display device 30, and an ultrasonic image processing device 100.

The ultrasonic irradiation device 10 may be a device for irradiating ultrasound. In this case, the ultrasonic irradiation device 10 may include a handpiece or an irradiation head equipped with a transducer. However, the present disclosure is not limited thereto, and the ultrasonic irradiation device 10 may be any device capable of irradiating ultrasound.

The ultrasonic imaging device 20 may obtain an ultrasonic image and transmit the ultrasonic image to the ultrasonic image processing device 100. In this case, the ultrasonic imaging device 20 may include a probe, and the probe may be mounted on one side of the ultrasonic irradiation device 10. For example, the probe may be mounted on a center portion of the irradiation head of the ultrasonic irradiation device 10. However, the present disclosure is not limited thereto, and the ultrasonic imaging device 20 may be any device capable of obtaining an ultrasonic image.

The ultrasonic image processing device 100 may perform operations in relation to a processing of an ultrasonic irradiation signal and a processing of an ultrasonic image. In this case, the ultrasonic image processing device 100 may include a memory 110, a processor 120, and a communication module 130.

The communication module 130 may perform communication with the ultrasonic irradiation device 10, the ultrasonic imaging device 20, and the display device 30. The communication module 130 may receive an ultrasonic image from the ultrasonic imaging device 20. The communication module 130 may include at least one of a wired communication module or a wireless communication module.

The wired communication module may include various cable communication modules such as Universal Serial Bus (USB), High Definition Multimedia Interface (HDMI), Digital Visual Interface (DVI), recommended standard 232 (RS-232), power line communication, or plain old telephone service (POTS) as well as various wired communication modules such as a Local Area Network (LAN) module, a Wide Area Network (WAN) module, or a Value Added Network (VAN) module.

The wireless communication module may include a wireless communication module that supports various wireless communication schemes such as Global System for Mobile Communication (GSM), Code Division Multiple Access (CDMA), Wideband Code Division Multiple Access (WCDMA), universal mobile telecommunications system (UMTS), Time Division Multiple Access (TDMA), Long Term Evolution (LTE), 4G, 5G, 6G, and the like as well as a Wi-Fi module and a Wireless broadband module.

The memory 110 may storing algorithm for controlling operations of the elements in the device and data for a program that reproduces the algorithm. The processor 120 may perform the operations described above by using the data stored in the memory 110. Here, the memory 110 and the processor 120 may be implemented in separated chips, respectively. Alternatively, the memory 110 and the processor 120 may be implemented in a single chip.

The memory 110 may store data that support various functions of the device, programs for operating the elements in the device, input/output data, a plurality of application programs (or applications) executed in the device, and data and commands for operating the device. At least a part of the application programs may be downloaded from an external server via a wireless communication.

The memory 110 may include at least a type of storage medium of flash memory type, hard disk type, Solid State Disk (SSD) type, Silicon Disk Drive (SDD) type, multimedia card micro type, memory of card type (e.g., SD or XD memory, etc.), (RAM random access memory), static random access memory (SRAM), read-only memory (ROM), electrically erasable programmable read-only memory (EE-PROM), programmable read-only memory (PROM), magnetic memory, magnetic disk, and optical disk.

The memory 110 may store data in relation to a processing of an ultrasonic irradiation signal and a processing of an ultrasonic image. The processor 120 may control operations in relation to the processing of an ultrasonic irradiation signal and the processing of an ultrasonic image.

The processor 120 may receive an ultrasonic image from the ultrasonic imaging device 20 and extract an irradiation area image for a region of interest (ROI) in the ultrasonic image of the ultrasonic imaging device associated with an ultrasonic irradiation signal of the ultrasonic irradiation device 10. In this case, the processor 120 may extract the irradiation area image based on an amplitude and phase data. For example, the processor 120 may extract the irradiation area image based on In-phase Quadrature (IQ) data.

The processor 120 may correct the irradiation area image based on a variation amount of the ultrasonic irradiation signal in the irradiation area image in a state of focused ultrasound of the ultrasonic irradiation device 10. In this case, when the processor 120 corrects the irradiation area image, the processor 120 may correct a brightness of the irradiation area image to a preset level. In addition, the processor 120 may correct an edge of the irradiation area image to a preset level when the processor 120 corrects the irradiation area image.

The processor 120 may control the display device 30 to display the corrected irradiation area image on the display device 30. In this case, the processor 120 may further control the display device 30 to display a degeneration area image in the corrected irradiation area image on the display device 30.

FIGS. 3 to 9 are diagrams illustrating an ultrasonic image processing process according to the present disclosure.

Referring to FIG. 3 to FIG. 9, the ultrasonic image processing method may include a reception operation S300, an extraction operation S310, a determination operation S320, a correction operation S330, and a control operation S340.

In the reception operation S300, an ultrasonic image may be received from the ultrasonic imaging device 20 through the communication module 130 (operation S300).

In the extraction operation S310, the processor 120 may extract an irradiation area image for a region of interest (ROI) in the ultrasonic image of the ultrasonic imaging device 20 associated with an ultrasonic irradiation signal of the ultrasonic irradiation device 10 (operation S310).

Figure 4:
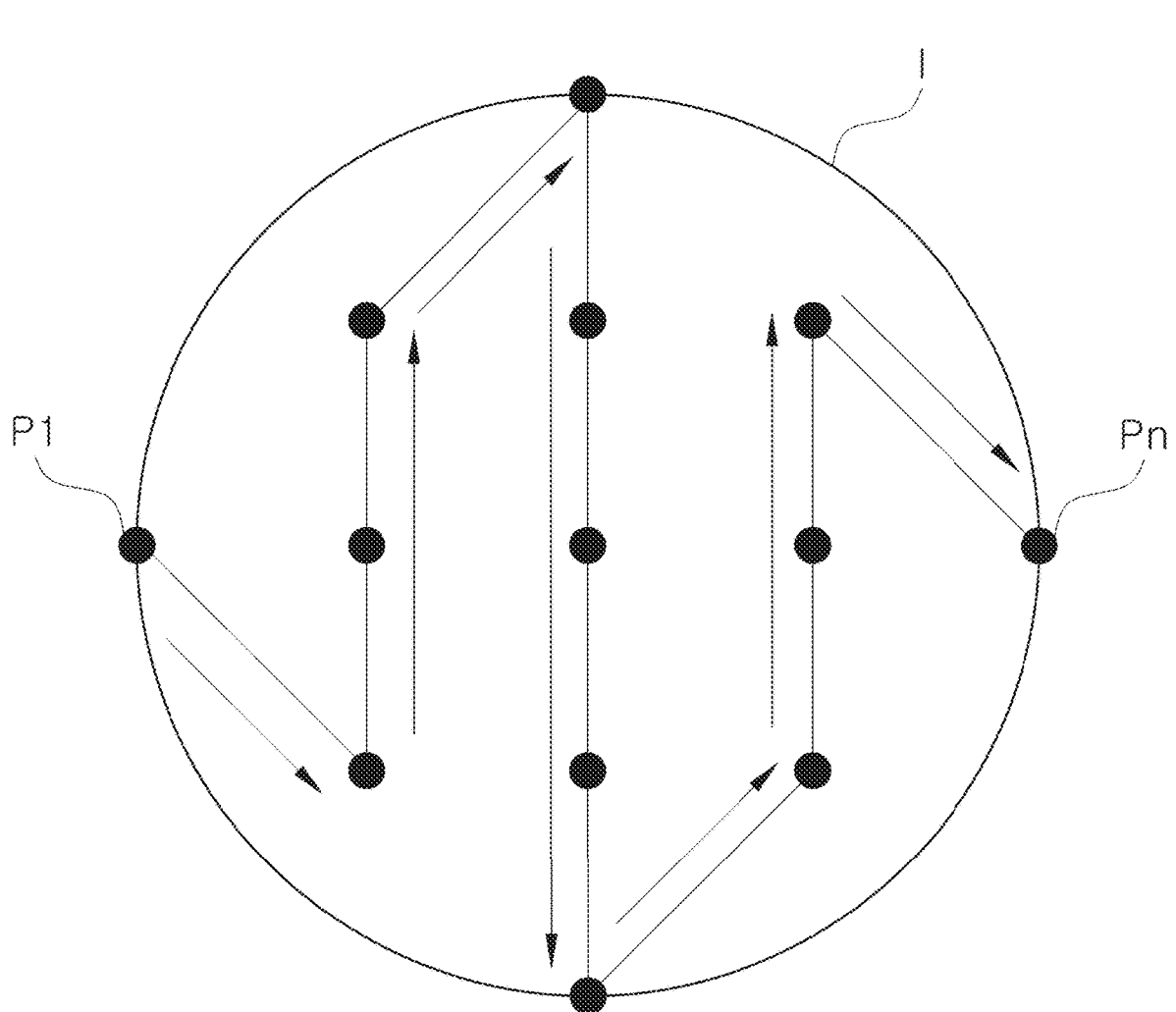

Here, as shown in FIG. 4, the ultrasonic irradiation device 10 may output the ultrasonic irradiation signal corresponding to the ultrasonic irradiation position from an ultrasonic irradiation start point P1 to an ultrasonic irradiation end point Pn, and the ultrasonic imaging device 20 may output an ultrasonic image I associated with the ultrasonic irradiation signal. For example, the ultrasonic irradiation device 10 may irradiate ultrasound according to an area of the myoma from the ultrasonic irradiation start point P1 to the ultrasonic irradiation end point Pn to necrotize the myoma. The ultrasonic irradiation device 10 may necrotize the myoma by accumulating heat while moving from the ultrasonic irradiation start point P1 to the ultrasonic irradiation end point Pn. In this case, the ultrasonic irradiation device 10 may include a handpiece or an irradiation head equipped with a transducer. In addition, the ultrasonic imaging device 20 may obtain an ultrasonic image. Here, the ultrasonic imaging device 20 may include a probe, and the probe may be mounted on one side of the ultrasonic irradiation device 10. For example, the probe may be mounted on a center portion of the irradiation head of the ultrasonic irradiation device 10.

In this case, the processor 120 may extract the irradiation area image based on an amplitude and phase data. For example, the processor 120 may extract the irradiation area image based on In-phase Quadrature (IQ) data. Here, the IQ Data may intuitively represent the amplitude and the phase data. In this case, the IQ Data may also derive a value for frequency movement since a phase component is known. Since the processor 120 based on the IQ data may even perform IQ processing with beamforming data when processing with the IQ Data, data throughput may also be reduced. In addition, the processor 120 may extract a pre-irradiation area image for the region of interest. In this case, the processor 120 may use the extracted pre-irradiation area image data as a default reference value.

In the determination operation, the processor 120 may determine whether the ultrasonic irradiation device 10 is in the state of focused ultrasound, based on a variation amount of the ultrasonic irradiation signal in the irradiation area image (operation S320). At this time, in the case that there is a variation amount of the ultrasonic irradiation signal, the processor 120 may determine that the ultrasonic irradiation device 10 is in the state of focused ultrasound, and in the case that there is no variation amount of the ultrasonic irradiation signal, the processor 120 may determine that the ultrasonic irradiation device 10 is in the state of non-focused ultrasound. For example, the processor 120 may check a presence of a variation amount of an ultrasonic echo signal. Here, the echo may indicate a degree of color of the lesion seen on the ultrasonic screen.

In this case, if there is no variation amount of the ultrasonic irradiation signal, the processor 120 may notify a warning message indicating the state of non-focused ultrasound through at least one of the ultrasonic irradiation device 10 or the display device 30, and may stop the use of the ultrasonic irradiation device 10. Meanwhile, if there is a variation amount of the ultrasonic irradiation signal, the processor 120 may notify the state of focused ultrasound through at least one of the ultrasonic irradiation device 10 or the display device 30. In addition, if there is a variation amount of the ultrasonic irradiation signal, the processor 120 may display the variation amount of the ultrasonic echo signal.

In addition, the processor 120 may identify the signal variation amount (Echo Change) before ultrasound is irradiated and the signal variation amount after ultrasound is irradiated in the irradiation area image, based on In-phase Quadrature (IQ) data, and output the signal variation amount for each operation in a time domain and a frequency domain. Here, the signal variation amount before ultrasound is irradiated may have a small amplitude value due to a low reflection coefficient of the tissue, and the signal variation amount after ultrasound is irradiated may have a great amplitude value due to a great reflection coefficient of the tissue. In this case, as shown in FIG. 5, the processor 120 may output an amplitude variation amount S by comparing amplitudes before and after ultrasonic is irradiated for each time region based on the IQ Data. For example, the processor 120 may have an amplitude value of 10 mVpp during one time of ultrasonic irradiation, and an amplitude value of 20 mVpp during two times of ultrasonic irradiation. In this way, the processor 120 may determine the signal variation amount of the tissue that becomes hard while being deformed due to the ultrasonic irradiation. In addition, as shown in FIGS. 6A and 6B, the processor 120 may analyze a frequency region of the frequency domain by fast Fourier transforming (FFT) the signal for each time region of the time domain, and output frequency components f0 to f4 and amplitude values S2 to S7 associated with the frequency components f0 to f4 based on the analyzed frequency region.

In addition, the processor 120 may further control the display device 30 to display the signal variation amount for each operation which is output in the time domain and the frequency domain on the display device 30. In this case, the processor 120 may display, for each operation, the amplitude variation amount obtained by comparing the amplitudes before the ultrasonic irradiation and after the ultrasonic irradiation for each time region, and may display, for each operation, the amplitude value associated with the frequency component based on the analyzed frequency region.

Figures 7A, 7B:
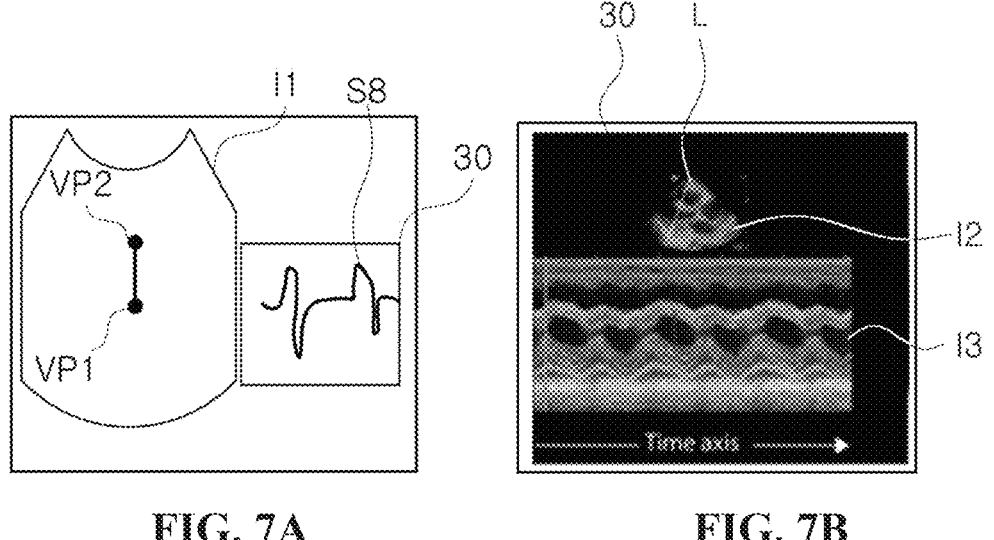

For example, as shown in FIG. 7A, the processor 120 may control the display device 30 to display a signal variation amount S8 for 2D-shaped ultrasonic irradiation points VP1 to VP2 corresponding to a B mode (brightness mode) selected in an irradiation area image I1 through the display device 30 as an irradiation area image corresponding to an M mode (motion mode). For another example, as shown in FIG. 7B, the processor 120 may control the display device 30 to display a portion designated by a scan line L (ultrasound line) in a 2D-shaped irradiation area image 12 corresponding to the above B mode (brightness mode) through the display device 30 as an irradiation area image I3 corresponding to the M mode (motion mode) in a time axis direction. Here, the irradiation area image I3 corresponding to the M mode may intuitively display the variation amount in the time axis direction. In this case, the processor 120 may control the display device 30 to designate a focused area by the scan line L (ultrasound line), compare the signal before ultrasonic irradiation with the signal under ultrasonic irradiation based on the designated scan line L (ultrasound line), and receive the signal variation amount according to the comparison result and display it as an irradiation area image through the display device 30.

In the correction operation, the processor 120 may correct the irradiation area image in a state of focused ultrasound of the ultrasonic irradiation device 10 (operation S330).

Figure 8:
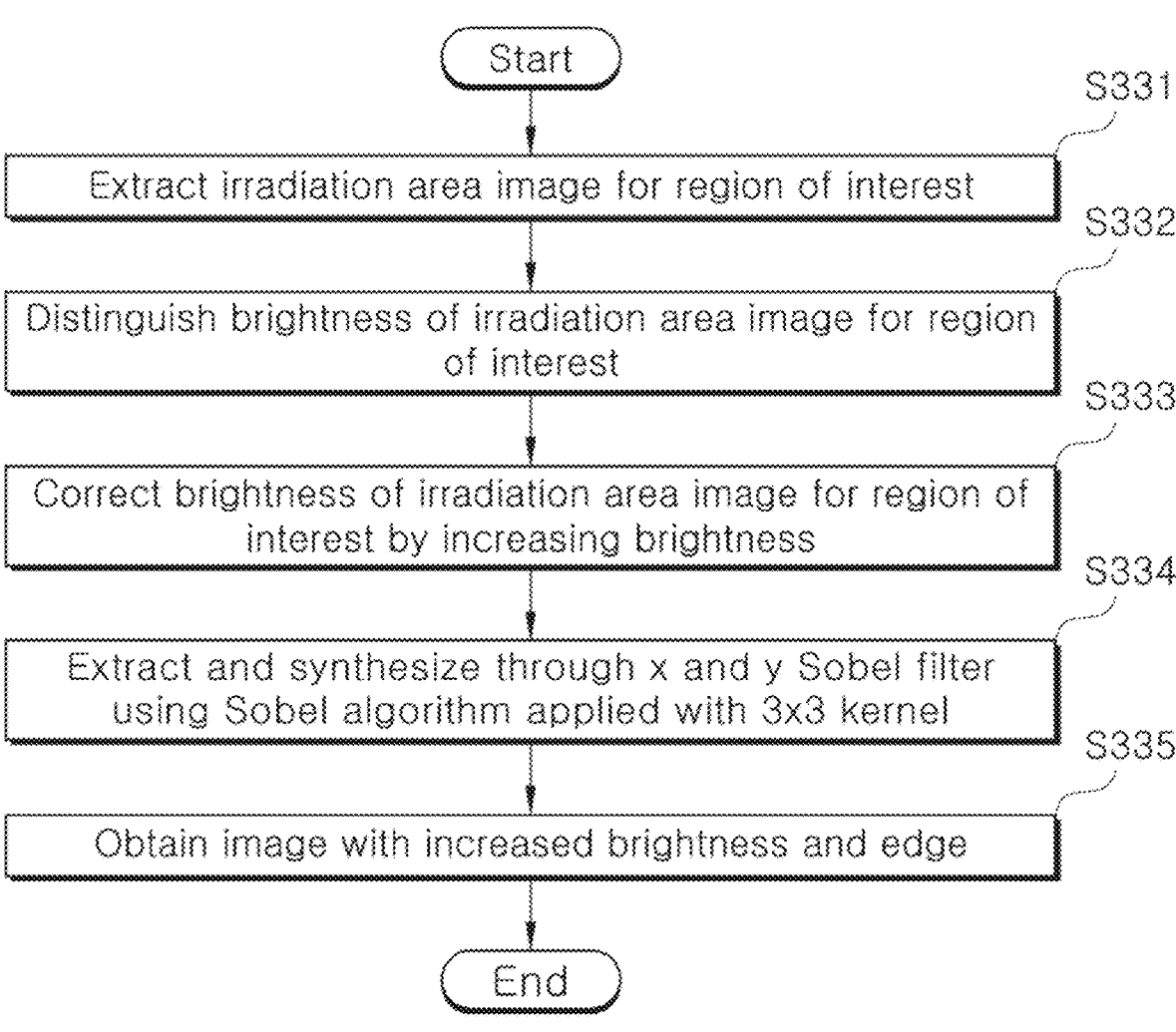

In one example, when correcting the irradiation area image, the processor 120 may correct a brightness of the irradiation area image in a preset level. Here, as shown in FIG. 8, the processor 120 may extract the irradiation area image for a region of interest (ROI) (operation S331) and distinguish the brightness of the irradiation area image for the region of interest (ROI) (operation S332).

Thereafter, the processor 120 may correct the brightness of the irradiation area image for the region of interest (ROI) by increasing the brightness to a preset level (operation S333). Here, the process of correcting the brightness of the irradiation area image by distinguishing and increasing it refers to a process of making the distinction clearer by increasing the distinction between black and white within the image.

In this case, the processor 120 may extract a histogram range on a black-and-white channel as a method for distinguishing and increasing the brightness of the irradiation area image. Here, the histogram may be a graphical representation of a degree of distribution of brightness values in the image, and the extraction of the histogram range may be extracting a distribution of brightness values distributed from black to white. That is, the processor 120 may determine whether a currently visible image is too bright, too dark, or appropriate through the extraction of the histogram range. For example, the processor 120 may extract the histogram range in a preset 5% to 95% section in an image stretching method so that the irradiation area image is clearly seen. However, the present disclosure is not limited thereto, and the processor 120 may extract the histogram range to another section by setting a parameter suitable for the condition of the irradiation area image.

Thereafter, when correcting the irradiation area image, the processor 120 may correct the edge, which is a point where the change in brightness is great based on the brightness of the irradiation area image, to a preset level. Here, the processor 120 may extract and synthesize through x and y Sobel filter using a Sobel algorithm applied with a 3×3 kernel (operation S334). In this case, the Sobel algorithm may highlight and display the boundary line seen in the irradiation area image, adjust the values of the 3×3-sized matrix (kernel), and detect the variation amount in each direction based on the adjusted values of the 3×3-sized matrix (kernel). In addition, the Sobel filter may extract an image with highlighted X-direction boundary line and an image with highlighted y-direction boundary line and synthesize the two images to generate a synthesized image with highlighted boundary lines in all directions.

Later, the processor 120 may synthesize the original irradiation area image and the Sobel filter and obtain an image with increased brightness and edge (operation S335). In this case, the processor 120 may obtain a sharp image in which the boundary line is revived from the original irradiation area image and synthesize the original irradiation area image and the Sobel filter to acquire the image with increased brightness and edge.

In the control operation, the processor 120 may control the display device 30 to display the corrected irradiation area image on the display device (operation S340). In this case, the processor 120 may further control the display device 30 to display a degeneration area image in the corrected irradiation area image on the display device 30. Here, the display device 30 may visualize the area being degenerated in the region of interest. In this case, a user may accurately identify the area being degenerated and the area where ultrasound is focused.

Figure 9:
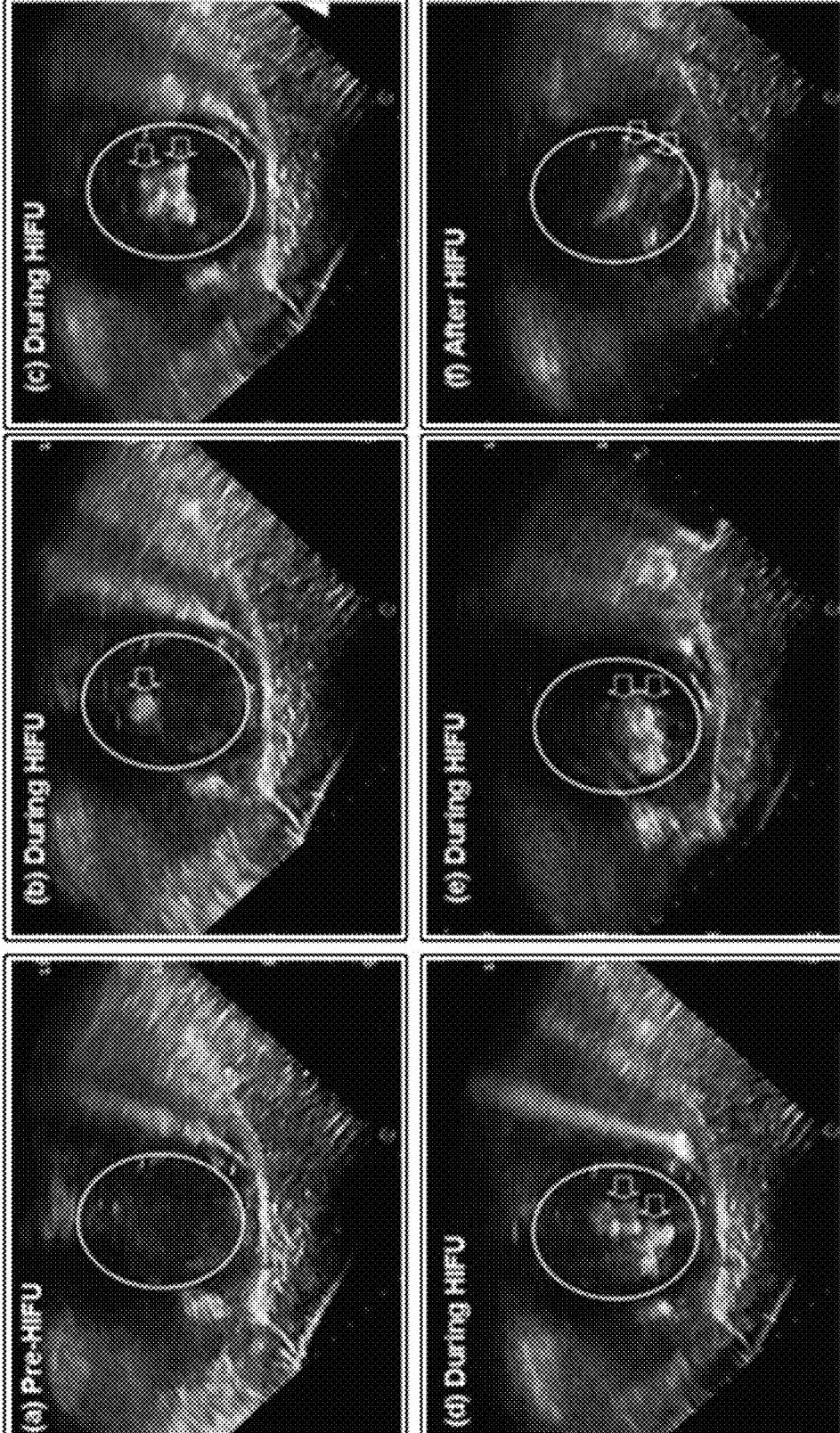

For example, as shown in (a) of FIG. 9, the display device 30 may display an image before the ultrasonic irradiation, and as shown in (b) to (e), the display device 30 may display an image in which the degeneration of the myoma in the corrected irradiation area image increases from operation (b) to operation (e) during the ultrasonic irradiation. In this case, the ultrasonic irradiation device 10 may maintain a focusing depth and a focusing time of ultrasound in the same state to necrotize the myoma, and may irradiate ultrasound according to an area of the myoma from the ultrasonic irradiation start point P1 (see FIG. 4) to the ultrasonic irradiation end point Pn (see FIG. 4). The ultrasonic irradiation device 10 may necrotize the myoma by accumulating heat while moving from the ultrasonic irradiation start point P1 (see FIG. 4) to the ultrasonic irradiation end point Pn (see FIG. 4). Here, as shown in (f), since the display device 30 concentrates a lot of heat in the middle, the myoma is more necrotic in the Z-axis direction at the ultrasonic irradiation points located in the middle rather than at the ultrasonic irradiation start point P1 (see FIG. 4) and the ultrasonic irradiation end point Pn (see FIG. 4), and the final degenerated shape may be displayed in a spherical shape. In this case, before ultrasonic irradiation, the tissue of the myoma is in a soft state and is marked in black, and during ultrasonic irradiation, the tissue of the myoma is necrotic, hardened, and may be marked in white.

As such, according to the embodiment of the present disclosure, since the position on which ultrasound is focused and the process of degenerating tumors are efficiently monitored, a safety accident caused by inaccuracies in ultrasonic irradiation and focusing can be prevented while improving the accuracy of ultrasonic irradiation and focusing.

At least one element may be added or deleted in response to the performance of the elements shown in FIG. 1, FIG. 2, FIG. 4 to FIG. 7B, and FIG. 9. In addition, it will be easily understood by those skilled in the art that the relative positions of elements may be changed in response to the performance or structure of the system.

Figure 3:
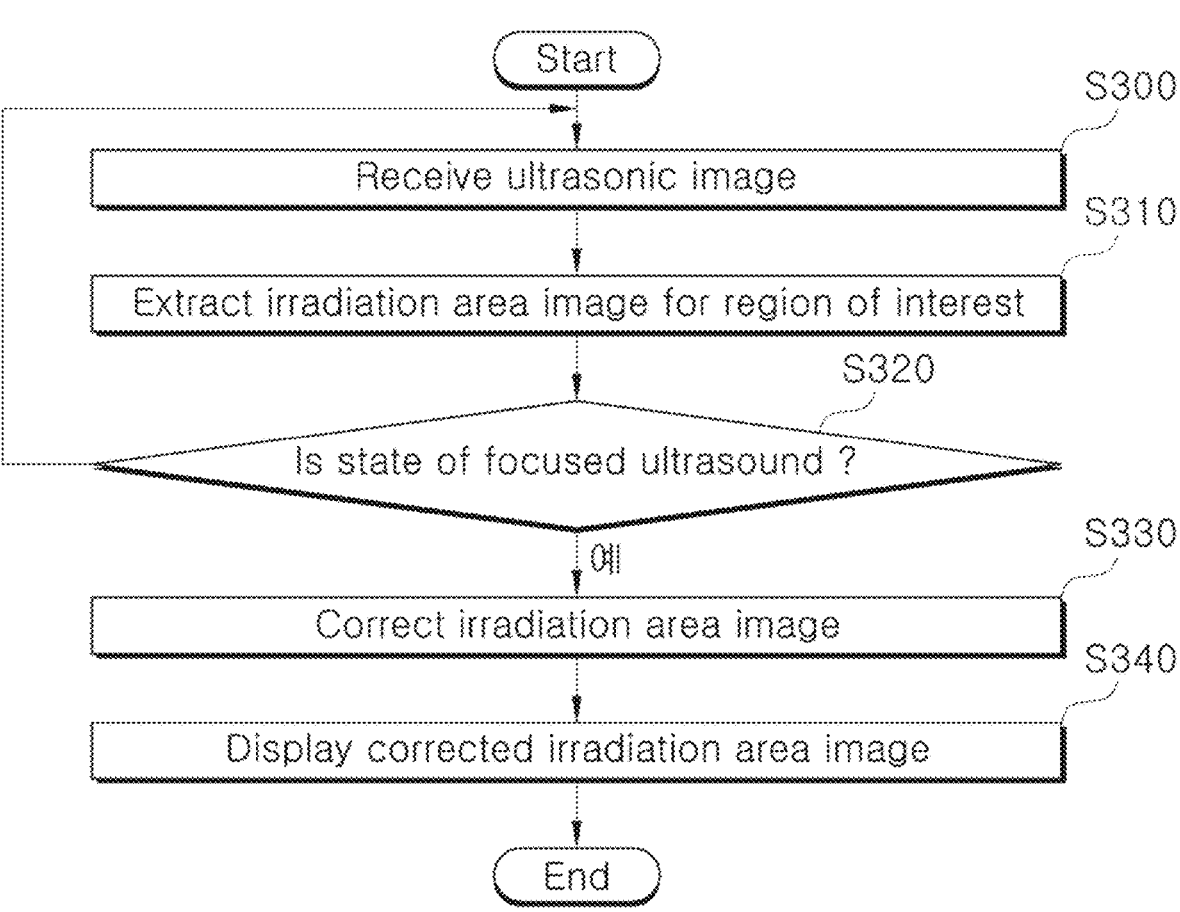

FIG. 3 and FIG. 8 illustrate that multiple operations are performed sequentially, but this is merely exemplary description of the technical concept of this embodiment, and those skilled in the art to which this embodiment belongs may change the order described in FIG. 3 and FIG. 8 or may variously modify to execute one or more of multiple operations in parallel within the scope not departing from the essential characteristics of this embodiment.

Meanwhile, the disclosed embodiments may be implemented in the form of a recoding medium that stores commands executable by a computer. The commands may be stored in the form of program codes, and when the commands are executed by the processor, the commands may generate a program module and perform the operations of the disclosed embodiments. The recording medium may be implemented with a computer-readable recording medium.

The computer-readable recording medium may include all types of recording media in which the commands interpretable by a computer are stored. For example, the recording medium may include Read Only Memory (ROM), Random Access Memory (RAM), magnetic tape, magnetic disk, flash memory, optical data storage device, and the like.

While the inventive concept has been described with reference to embodiments, it will be apparent to those skilled in the art that various changes and modifications may be made without departing from the spirit and scope of the inventive concept. Therefore, it should be understood that the above embodiments are not limiting, but illustrative.

Advantageous Effects

According to the technical solution to solve the problem according to the present disclosure, there is an effect that the position on which ultrasound is focused and the process of degenerating tumors are efficiently monitored, and thus a safety accident caused by inaccuracies in ultrasonic irradiation and focusing can be prevented while improving the accuracy of ultrasonic irradiation and focusing.

The advantages of the present disclosure are not limited to the above-mentioned advantages, and other advantages, which are not specifically mentioned herein, will be clearly understood by those skilled in the art from the following description.

What is claimed is:

1. An ultrasonic image processing device, comprising:
   a communication interface configured to receive ultrasonic images from an ultrasonic imaging device; and
   a processor configured to:
   extract irradiation area images from the received ultrasonic images, wherein the extracted irradiation area images correspond to a region of interest (ROI) to be irradiated by an ultrasonic irradiation device for treatment of a tumor, wherein the extracted irradiation area images include a first extracted irradiation area image corresponding to the ROI prior to irradiation by the ultrasonic irradiation device and a second extracted irradiation area image corresponding to the ROI after irradiation by the ultrasonic irradiation device has begun;
   determine that the second extracted irradiation area image shows that the ROI is being irradiated by the ultrasonic irradiation device based on a change in amplitude between the first extracted irradiation area image and the second extracted irradiation area image;
   based on determining that the second extracted irradiation area image shows that the ROI is being irradiated by the ultrasonic irradiation device, correct brightness of the second extracted irradiation area image by increasing the brightness of the second extracted irradiation area image to a preset level to generate a corrected irradiation area image; and
   control a display device to display the corrected irradiation area image and a degeneration area image in the corrected irradiation area image on the display device, wherein the degeneration area image shows degeneration of the tumor.

2. The ultrasonic image processing device of claim 1, wherein the processor is configured to extract the irradiation area images based on amplitude and phase data.

3. The ultrasonic image processing device of claim 1, wherein the processor is configured to correct an edge of the second extracted irradiation area image to the preset level.

4. An ultrasonic image processing method, comprising:
   receiving, by an ultrasonic image processing device, ultrasonic images from an ultrasonic imaging device;
   extracting, by the ultrasonic image processing device, irradiation area images from the received ultrasonic images, wherein the extracted irradiation area images correspond to a region of interest (ROI) to be irradiated by an ultrasonic irradiation device for treatment of a tumor, wherein the extracted irradiation area images include a first extracted irradiation area image corresponding to the ROI prior to irradiation by the ultrasonic irradiation device and a second extracted irradiation area image corresponding to the ROI after irradiation by the ultrasonic irradiation device has begun;
   determining, by the ultrasonic image processing device, that the second extracted irradiation area image shows that the ROI is being irradiated by the ultrasonic irradiation device based on a change in amplitude between the first extracted irradiation area image and the second extracted irradiation area image;
   based on determining that the second extracted irradiation area image shows that the ROI is being irradiated by the ultrasonic irradiation device, correcting, by the ultrasonic image processing device, brightness of the second extracted irradiation area image by increasing the brightness of the second extracted irradiation area image to a preset level to generate a corrected irradiation area image; and
   controlling, by the ultrasonic image processing device, a display device to display the corrected irradiation area image and a degeneration area image in the corrected irradiation area image on the display device, wherein the degeneration area image shows degeneration of the tumor.

5. The method of claim 4, wherein correcting the second extracted irradiation area image includes correcting an edge of the second extracted irradiation area image to the preset level.

6. A system, comprising:
   an ultrasonic irradiation device;
   an ultrasonic imaging device;
   a display device; and
   an ultrasonic image processing device configured to communicate with the ultrasonic irradiation device, the ultrasonic imaging device, and the display device;

wherein the ultrasonic image processing device is configured to:
   receive ultrasonic images from the ultrasonic imaging device;
   extract irradiation area images from the received ultrasonic images, wherein the extracted irradiation area images correspond to a region of interest (ROI) to be irradiated by the ultrasonic irradiation device for treatment of a tumor, wherein the extracted irradiation area images include a first extracted irradiation area image corresponding to the ROI prior to irradiation by the ultrasonic irradiation device and a second extracted irradiation area image corresponding to the ROI after irradiation by the ultrasonic irradiation device has begun;
   determine that the second extracted irradiation area image shows that the ROI is being irradiated by the ultrasonic irradiation device based on a change in amplitude between the first extracted irradiation area image and the second extracted irradiation area image;
   based on determining that the second extracted irradiation area image shows that the ROI is being irradiated by the ultrasonic irradiation device, correct brightness of the second extracted irradiation area image by increasing the brightness of the second extracted irradiation area image to a preset level to generate a corrected irradiation area image; and
   control the display device to display the corrected irradiation area image and a degeneration area image in the corrected irradiation area image on the display device, wherein the degeneration area image shows degeneration of the tumor.

7. The system of claim 6, wherein the ultrasonic image processing device is configured to extract the second extracted irradiation area image based on amplitude and phase data.

8. The system of claim 6, wherein the ultrasonic image processing device is configured to correct an edge of the second extracted irradiation area image to the preset level.

9. The method of claim 4, wherein extracting the second extracted irradiation area image is based on amplitude and phase data.

10. The ultrasonic image processing device of claim 1, wherein correcting the brightness of the second extracted irradiation area image uses a histogram representing a distribution of brightness values in the second extracted irradiation area image.

11. The ultrasonic image processing device of claim 10, wherein the histogram is extracted on a black-and-white channel.

* * * * *